(12) United States Patent
Acharya et al.

(10) Patent No.: US 7,019,117 B2
(45) Date of Patent: Mar. 28, 2006

(54) SIZE ENHANCED HEMOGLOBINS: SURFACE DECORATION AND CROSSLINKING OF THE PROTEIN WITH POLYOXY ALKYLENE GLYCOLS

(75) Inventors: Seetharama A. Acharya, Cresskill, NJ (US); Belur N. Manjula, Cresskill, NJ (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 483 days.

(21) Appl. No.: 10/198,732

(22) Filed: Jul. 18, 2002

(65) Prior Publication Data
US 2004/0002443 A1 Jan. 1, 2004

Related U.S. Application Data

(60) Provisional application No. 60/306,623, filed on Jul. 19, 2001.

(51) Int. Cl.
*C07K 14/805* (2006.01)

(52) U.S. Cl. .......................... 530/385; 530/402; 514/2
(58) Field of Classification Search ................ 530/385, 530/402; 514/2
See application file for complete search history.

(56) References Cited

U.S. PATENT DOCUMENTS

| 4,301,144 | A | | 11/1981 | Iwashita et al. |
| 4,412,989 | A | * | 11/1983 | Iwashita et al. ............ 514/762 |
| 4,670,417 | A | | 6/1987 | Iwasaki et al. |
| 5,234,903 | A | | 8/1993 | Nho et al. |
| 5,312,808 | A | | 5/1994 | Shorr et al. |
| 5,585,484 | A | | 12/1996 | Acharya et al. |

FOREIGN PATENT DOCUMENTS

WO    WO 94/04193    3/1994

OTHER PUBLICATIONS

Rao et al. 'Amidation of Basic Carboxyl Groups of Hemoglobin,' Methods in Enzymology. vol. 231. pp. 246-267. 1994.*

Acharya, A.S. and Sussman, L.G., "The Reversibility of the Ketoamine Linkages of Aldoses with Proteins"; The Journal of Biological Chemistry, Apr. 10, 1984, pp. 4372-4378, vol. 259, No. 7.

Acharya, A.S., et al., "Aldimine to Ketoamine Isomerization (Amadori Rearrangement) Potential at the Individual Nonenzymic Glycation Sites of hemoglobin A: Preferential Inhibition of Glycation by Nucleophiles at Sites of Low Isomerization Potential"; Journal of Protein Chemistry, 1991, pp. 345-358, vol. 10, No. 3.

Acharya, A.S., et al., "Schiff Base Addicts of Glyceraldehyde with Hemoglobin"; The Journal of Biological Chemistry, Feb. 25, 1983, pp. 2296-2302, vol. 258, No. 4.

Manjula, B.N., et al., "Cys-93-beta-Succinimidophenyl Polyethylene Glycol 2000 Hemoglobin A"; The Journal of Biological Chemistry, Feb. 25, 2000, pp. 5527-5534, vol. 275, No. 8.

Nho, K., et al., "PEG-Hemoglobin: An Efficicent Oxygen-Delivery System In The Rat Exchange Transfusion And Hypovolemic Shock Models"; Art. Cells, Blood Subs., And Immob. Biotech., 1994, pp. 795-803, vol. 22(3).

(Continued)

*Primary Examiner*—Anish Gupta
(74) *Attorney, Agent, or Firm*—Amster, Rothstein & Ebenstein LLP (57) ABSTRACT

Novel modified hemoglobins comprising polyalkylene glycols and novel methods for making those hemoglobins are provided. One group of modified hemoglobins comprise polyalkylene glycols bonded to the hemoglobin with an amide linkage at Glu-43($\beta$). Additional polyalkylene glycols can also be bonded to the Glu-22($\beta$) and/or the Asp-47($\beta$). These hemoglobins are made by a novel amidation procedure. A second group of modified hemoglobins comprise a polyalkylene glycol covalently bonded to the hemoglobin at the $\alpha$-amino of a Val-1($\beta$) or a Val-1($\alpha$). Additional polyalkylene glycols can optionally be covalently bonded to a limited number of $\epsilon$-amino groups. This second group of hemoglobins is made using a novel reductive alkylation procedure. A third group of modified hemoglobins comprise a polyalkylene glycol bonded to a thiol group of the hemoglobin through a phenylsuccinimido linkage, wherein no polyalkylene glycol is bonded to a Cys-93($\beta$). This third group of modified hemoglobins is made by an improvement in a hemoglobin-polyalkylene linkage procedure utilizing thiolation-mediated maleimide chemistry.

22 Claims, 5 Drawing Sheets

OTHER PUBLICATIONS

Seetharam, R., et al., "Specific Modification of the Carboxyl Groups of Hemoglobin S"; The Journal of Biological Chemistry, Dec. 25, 1983, pp. 14810-14815, vol. 258, No. 24.

Vandegriff, K.D., et al., "Colloid osmotic properties of modified hemoglobins: chemically cross-linked versus polyethylene glycol surface-conjugated"; Biophysical Chemistry, 1997, pp. 23-30, vol. 69.

Winslow, R.M., et al., "Vascular resistance and the efficacy of red cell substitutes in a a rat hemorrhage model"; Journal of Applied Physiology, (1998, pp. 993-1003, vol. 85(3).

Xue, H. Wong, J.T.-F., "Preparation of Conjugated Hemoglobins"; Methods in Enzymology, 1994, pp. 308-322, vol. 231.

* cited by examiner

SIZE ENHANCED HEMOGLOBINS: SURFACE DECORATION AND CROSSLINKING OF THE PROTEIN WITH POLYOXY ALKYLENE GLYCOLS

CROSS-REFERENCE TO RELATED APPLICATION

This application claims the benefit of U.S. Provisional Application No. 60/306,623, filed Jul. 19, 2001.

BACKGROUND (1) Field of the Invention

The present invention generally relates to novel modified hemoglobin and novel methods for modifying hemoglobin. More specifically, the invention relates to novel hemoglobin compositions comprising polyalkylene glycols and methods for making those hemoglobin compositions.

(2) Description of the Related Art

References cited:

Acharya and Khandke, *J. Prot. Chem.* 8:231, 1989.
Acharya and Manning, *J. Biol. Chem.* 255:7218–24, 1980.
Acharya and Manning, *J. Biol. Chem.* 255:1406–12, 1980.
Acharya and Manning, *Proc. Natl. Acad. Sci. USA* 80:3590–94, 1983.
Acharya and Manjula, *Biochemistry* 26:3524, 1987.
Acharya and Nacharaju, In: Maillard reactions in chemistry, food and health; Labuza, T. P., Reineccius, G. A., Monnier, V., O'Brien, J., and Baynes, J., (eds). The Royal Society of Chemistry, Cambridge, UK, 1994.
Acharya and Seetharam, *Biochemistry* 25:4885–90, 1985.
Acharya and Sussman, *J. Biol. Chem.* 259:4372–78, 1984.
Acharya and Taniuchi, *J. Biol. Chem.* 251:6934–46, 1976.
Acharya and Taniuchi, *Mol. Cell. Biochem.* 44:129–48, 1982.
Acharya et al., *Ann. NY. Acad. Sci.* 565:349–50, 1989.
Acharya et al., *Biochemistry* 27:4522, 1987.
Acharya et al., *J. Prot. Chem.* 10:345, 1991.
Acharya et al., *J. Biol. Chem.* 258:2296–302, 1983.
Acharya et al., *J. Biol. Chem.* 260:6039, 1985.
Acharya et al., pp. 269–280 In Molecular Conformation and Biological Interactions (Balaram, P., and Ramaseshan, S., eds.) Indian Academy of Sciences, Bangalore, India, 1991.
Ajisaka and Iwashita, *Biochem. Biophys. Res. Commun.* 97:1076, 1980.
Bunn et al., *J. Exp. Med.* 129, 909–924, 1969.
Kluger et al., *Art. Cells, Blood Subs. Immob. Biotech.* 22:415–428, 1994.
Means and Feeney, *Anal. Chemistry* 224:1–16, 1995.
MacDonald and Pepper, *Meth. Enzymol* 231:287–308, 1994.
Manjula, et al., *Art. Cells, Blood Subs. Immob. Biotech.* 22:747–752, 1994.
Nacharaju and Acharya, pp. 96–103 In Nonenzymic glycosylation and browning of proteins. Srinivasan, A., and Abraham, E. C., (eds) University of Madras, Madras, India.
Nho et al., *Art. Cells. Blood. Sub. and Immob. Biotech.* 22:795–803, 1994.
Perumalsamy et al., *Blood* 92:11a, 1998.
Perutz, M. F., *Nature* (London) 228:726, 1970.
Perutz et al., *J. Mol. Biol.* 138:649, 1980.
Perutz et al., *J. Mol. Biol.* 183:491, 1983.
Rao and Acharya, *J. Prot. Chem.* 10:129–38, 1991.
Rao and Acharya, *Biochemistry* 31:7231–36, 1992.
Rao and Acharya, *Meth. Enzymol.* 231:246–64, 1994.
Rao et al., *J. Biol. Chem.* 270:19250–55, 1995.
Seetharam et al., *J. Biol. Chem.* 258:14810–15, 1983.
Shearwater Corporation catalog.
Simon and Konigsberg, *Proc. Natl. Acad. Sci. USA* 56:749–756, 1966.
Vandegriff et al., *Biophys. Chem.* 69:23–30, 1997.
Walder et al., *Meth. Enzymol.* 231:274–281, 1994.
Winslow et al., *J. Appl. Physiol.* 85: 993–1003, 1998.
Xue and Wong, *Meth. Enzymol.* 231:308–322, 1994.
U.S. Pat. No. 4,301,144.
U.S. Pat. No. 4,412,989.
U.S. Pat. No. 4,670,417.
U.S. Pat. No. 5,234,903.
U.S. Pat. No. 5,334,707.
U.S. Pat. No. 5,312,808.
U.S. Pat. No. 5,349,054.
U.S. Pat. No. 5,585,484.
WO 94/04193.

Hemoglobin (Hb) is the major constituent of the erythrocyte which carries oxygen from the lungs throughout the body. When contained in red blood cells, Hb exists as a tetramer structure composed of two oxygen linked $\alpha\beta$ dimers, each having a molecular weight of about 32 Kd. Each $\alpha$ and $\beta$ subunit of each dimer has a protein chain and a heme molecule.

The sequences of the $\alpha$ and $\beta$ protein chains are known. Hb is a potentially useful blood substitute for transfusions, and has been proposed as a reagent to trap nitric oxide in septic shocks, and to modulate tissue oxygenation during radiation therapy of cancer. Recombinant DNA technology also has afforded the generation of modified Hb with oxygen affinities modulated for special needs of individual therapeutic applications.

The potential use of Hb as blood substitutes in transfusions or other therapeutic applications, however, has been hampered by the short circulation half-life of Hb. In solution outside of the red blood cell, Hb readily dissociates from its tetrameric form into its dimers and even monomers, which are rapidly filtered through the kidneys. Accordingly, a multitude of methods for crossbridging Hb (e.g. bifunctional modification) and other means for increasing the hydrodynamic volume of Hb (e.g. monofunctional decoration) have been devised to limit or prevent the extravasation of Hb.

Simon and Konigsberg (1966) reports the use of bis(N-maleimidomethyl) ether (BME) to generate intramolecularly crosslinked Hb. Bunn et al. (1969) later reported that BME crosslinked Hb increased the half-life of Hb four-fold when infused into rats and dogs. However, the crosslinking of Hb with BME resulted in a concomitant increase in the oxygen affinity of Hb which prevented its use as a potential Hb-based oxygen carrier.

Xue and Wong (1994) describes many of the current methods for crosslinking Hb. These include the use of dextran, hydroxyethyl starch, inulin, polyvinylpyrrolidone, and polyethylene glycol as crosslinkers for Hb. Other crosslinkers include glycoaldehyde and glutaraldehyde (MacDonald and Pepper, 1994); bis(3,5-dibromosalicyl)fumarate (Walder, R. Y., et al., 1994); acyl phosphate esters (Kluger et al., 1994 U.S. Pat. No. 5,334,707); bissulfosuccinimidyl esters of aliphatic dicarboxylic acids (Manjula et al., 1994); and benzenepentacarboxylate (U.S. Pat. No. 5,349,054).

Nho et al. (1994) describes the monofunctional decoration of hemoglobin with polyethylene glycol. Similar modification of the hemoglobin molecule are described in U.S. Pat. Nos. 4,301,144; 4,412,989; 4,670,417; 5,234,903; and 5,312,808, and WIPO publication WO 94/04193.

The various modified hemoglobins described in the references cited above can be broadly grouped into three classes. (i) intramolecularly crossbridged Hb tetramers, (ii) inter and intra molecularly cross bridged Hb polymers, and (iii) Hb surface decorated with inert polymers such as polyethylene glycol (PEG). All these three classes of modified hemoglobins prevent glomerular filtration of acellular Hb and hence do not exhibit any nephrotoxicity that is associated with unmodified acellular Hb. However, the intrinsic propensity of Hb to bind nitric oxide, and hence its ability to influence vascular tone when present as an acellular component has been an obstacle to the widespread adoption of acellular Hb for therapeutic purposes. The different classes of modified Hb exhibit different degrees of vasoactivity. The intramolecularly crossbridged Hb, with its molecular size of 64,000 daltons, exhibited the highest vasoactivity, which is comparable to that of unmodified Hb. The intra and intermolecularly crossbridged species of Hb, with apparent molecular size of 200,000 to 300,000 exhibit a somewhat lowered vasoactivity relative to the parent Hb (or intramolecularly crossbridged HbA). The samples of Hb surface decorated with PEG chains with an apparent molecular size of 275,000 daltons or higher do not exhibit any vasoactivity. Thus, the increased molecular size of Hb appears to have reduced the vasoactivity of the product, presumably minimizing the extravasation of the sample into the interstitial space. This observation has presented a new approach to overcome the vasoactivity mediated toxicity of acellular Hb, distinct from approaches under development to engineer the Hb molecule through site directed mutagenesis to suppress the affinity of heme towards nitric oxide. The higher viscosity and the colloidal osmotic pressure of the solutions of surface decorated Hb appears to have other beneficial effects as well (Vandegriff et al., 1997; Winslow et al., 1998).

The surface decorated Hb investigated to date carry about ten PEG-5000 chains per tetramer (total mass of about 50,000 daltons of PEG per tetramer). The PEG-chains in this sample are linked to the surface α and/or ε-amino groups of Hb through isopeptide linkage (succinimidyl chemistry based PEGalation). Such preparations of surface decorated Hb do not increase the blood pressure, systemic vascular resistance remained unchanged, and tissue oxygenation are maintained at a level comparable to that of blood, even though the oxygen affinity of these preparations are higher than that of erythrocytes (Winslow et al., 1998).

One of the limitations of the above-described succinimidyl chemistry for surface decoration of Hb with PEG chains at the amino groups of Hb, is that the isopeptide linkage generated between Hb and the PEG-molecule does not carry the original positive charge of the amino (α or ε) of Hb. To overcome this limitation of earlier surface decoration chemistry, a novel protocol was recently developed to attach PEG-chains to Hb using the ε-amino groups of its surface Lys residues wherein the Hb still retains the original positive charge of the amino groups (U.S. Pat. No. 5,585,484). This involves amidination of the ε-amino groups of Hb by iminothiolane to introduce sulfhydryl groups on to the protein, which are subsequently targeted as the modification sites for PEGalation using maleimide chemistry-based PEG reagents. This approach has at least two additional specific advantages over the previously used succinimidyl chemistry: (1) the very high reactivity and selectivity of the maleimide based reagents to the sulfhydryl groups facilitates the near quantitative modification of the thiols with a limited excess of the reagents (in this case maleidophenyl PEG-chains), and (2) the thiol group of iminothiolane is latent and is generated only in situ as a consequence of the reaction of the reagent with the protein amino groups. Accordingly, Hb can be incubated simultaneously with the thiolating and the PEGalating reagents for surface decoration with PEG-chains.

Despite its advantages, the thiolation mediated, maleimide chemistry based surface decoration procedure described in U.S. Pat. No. 5,585,484 results in the modification of Cys-93(β) by the maleidophenyl PEG. This modification leads to an increase in the oxygen affinity of Hb.

Most of the known compounds used to modify Hb are difficult to synthesize, do not modify Hb in an efficient manner, cannot be manipulated quantitatively to form the desired modification, and/or lower or raise the oxygen affinity of the modified hemoglobin. Accordingly, there exists a need for new synthetic compounds, and new methods which can modify hemoglobin in an efficient and focused manner, and do not substantially affect the oxygen affinity of the modified hemoglobin. The present invention satisfies this need.

SUMMARY OF THE INVENTION

Accordingly, the inventors have succeeded in developing three novel methods for creating novel modified hemoglobins comprising polyalkylene glycols. The hemoglobins provide certain properties that are superior to other modified hemoglobins.

Thus, one embodiment of the present invention is directed to a hemoglobin comprising a polyalkylene glycol, wherein the polyalkylene glycol is a polypropylene glycol or a polyethylene glycol (PEG), and the polyalkylene glycol is covalently bonded to the hemoglobin with an amide linkage at a Glu-43(β). Preferably, the polyalkylene glycol is a PEG, and the hemoglobin is a hemoglobin A. In other preferred embodiments, the polyalkylene glycol is a PEG, and the hemoglobin further comprises a second PEG wherein the second PEG is covalently bonded to a Glu-22(β) with an amide linkage. In some aspects of these embodiments, the polyalkylene glycol is a PEG, and the PEG does not crosslink the hemoglobin intramolecularly or intermolecularly. Preferably, these hemoglobins have at least 6 PEGs bonded to the hemoglobin through an amide linkage. In other aspects of these embodiments, the polyalkylene glycol is a PEG, and the PEG intramolecularly crosslinks the hemoglobin, or intermolecularly crosslinks the hemoglobin with a second hemoglobin.

Other embodiments of the invention are directed to a hemoglobin composition comprising hemoglobin (Hb) decorated with one or more PEG molecules. In these embodiments, the Hb-PEG has the formula wherein n is an integer from about 125 to about 500, m is an integer from 1 to 10, W is NH or O, R is an amino acid side chain, R' is selected from the group consisting of OH, OCH$_3$, CH$_2$OH, CH$_2$OCH$_3$, CH$_2$CH$_2$OH, and CH$_2$CH$_2$OCH$_3$, and wherein at least one PEG is bonded to the Hb at Glu-43(β). Preferably, the Hb is a hemoglobin A, W is NH, n is about 125, m is 6–8, R is H or CH$_2$COOH, and R' is CH$_2$CH$_2$OCH$_3$.

Additional embodiments provide a hemoglobin composition comprising at least one hemoglobin molecule (Hb), crosslinked by one or more PEG molecules, wherein the crosslinked Hb has the formula wherein Hb and Hb' are the same or different hemoglobin molecule, n is an integer from about 15 to about 250, W and W' are each independently NH or O, R is an amino acid side chain, and HbA and/or HbA' is bonded to the PEG with an amide linkage at Glu-43($\beta$). Preferably, R is H or $CH_2COOH$, Hb and Hb' are different hemoglobin A tetramers, W and W' are both NH, and the PEG intermolecularly crosslinks HbA with HbA'.

In additional embodiments, the present invention is directed to a method of producing a hemoglobin comprising a polyalkylene glycol, wherein the polyalkylene glycol is polypropylene glycol or polyethylene glycol (PEG). The method comprises mixing in a suitable buffer (a) the hemoglobin, (b) a carbodiimide, and (c) a nucleophilic polyalkylene glycol with a terminal amine having a $pK_a$ below 9, and incubating the mixture under conditions and for a time sufficient for the polyalkylene glycol to covalently bond to the hemoglobin at Glu-43($\beta$). In preferred aspects of these embodiments, the polyalkylene glycol is a PEG, and 6 to 8 PEG molecules bind to the hemoglobin. In other preferred aspects, the hemoglobin is hemoglobin A, the buffer is MES buffer at pH 6–8, the carbodiimide is 1-ethyl-3-(3'-dimethylaminopropyl)carbodiimide, and the mixture further comprises N-hydroxysulfosuccinimide. Preferably, the carbodiimide is present in the mixture at about 10–50 mM.

In still other embodiments, the present invention is directed to a method of producing a hemoglobin comprising a polyethylene glycol (PEG). The method comprises mixing in a suitable buffer (a) the hemoglobin, (b) a carbodiimide, and (c) a nucleophilic PEG with a terminal amine having a $pK_a$ below 9, and incubating the mixture under conditions and for a time sufficient for the PEG to covalently bond to the hemoglobin at Glu-43($\beta$). In these embodiments, the nucleophilic PEG has the formula wherein n is an integer from about 125 to about 500, W is NH or O, R is an amino acid side chain, and R' is selected from the group consisting of OH, $OCH_3$, $CH_2OH$, $CH_2OCH_3$, $CH_2CH_2OH$, and $CH_2CH_2OCH_3$; preferably, the hemoglobin is a hemoglobin A, W is NH, n is about 125, R is H or $CH_2COOH$, and R' is $CH_2CH_2OCH_3$.

In other aspects of these methods, the nucleophilic PEG has the formula wherein n is an integer from about 15 to about 250, W and W' are each independently NH or O, and R and R' are each independently an amino acid side chain; preferably W and W' are both NH, and R or R' is each independently H or $CH_2COOH$.

The present invention is also directed to a hemoglobin comprising a polyalkylene glycol, wherein the polyalkylene glycol is polypropylene glycol or polyethylene glycol (PEG), and wherein the polyalkylene glycol is covalently bonded to the hemoglobin at the $\alpha$-amino of a Val-1($\beta$). Preferably, the polyalkylene glycol is a PEG, and the hemoglobin is hemoglobin A. In other preferred embodiments, the hemoglobin further comprises a second PEG wherein the second PEG is covalently bonded to the hemoglobin at the $\alpha$-amino of a Val-1($\alpha$). In some aspects of these embodiments, the polyalkylene glycol does not crosslink the hemoglobin intramolecularly or intermolecularly; in other aspects the polyalkylene glycol does crosslink the hemoglobin. In preferred embodiments, at least 4 polyalkylene glycols are bonded to the hemoglobin at an amino moiety.

In preferred embodiments, the invention is directed to a hemoglobin composition comprising hemoglobin A (HbA) decorated with one or more PEG molecules, wherein the HbA-PEG has the formula wherein p is an integer from 2 to 6, q is 1 or 2, n is an integer from about 125 to about 500, m is an integer from 1 to 10, and R is selected from the group consisting of OH, $OCH_3$, $CH_2OH$, $CH_2OCH_3$, $CH_2CH_2OH$, and $CH_2CH_2OCH_3$. Preferably, q is 1, n is about 125, m is 1–4, and R is $CH_2CH_2OCH_3$.

In other preferred embodiments the invention is directed to a hemoglobin composition comprising a hemoglobin (Hb) crosslinked by one or more PEG molecules, wherein the crosslinked Hb has the formula wherein Hb and Hb' are the same or different hemoglobin molecule, each p is independently an integer from 2 to 6, each q is 1 or 2, and n is an integer from about 15 to about 250. Preferably, q is 1. Hb and Hb' can be the same or different hemoglobin A tetramer.

The invention is also directed to a method of producing a hemoglobin comprising a polyalkylene glycol, wherein the polyalkylene glycol is a polypropylene glycol or a polyethylene glycol (PEG), and wherein the PEG is covalently bonded to the hemoglobin at the $\alpha$-amino of a Val-1($\beta$). The method comprises incubating the hemoglobin with a polyalkylene glycol aldehyde and a borohydride under conditions and for a time sufficient for the polyalkylene glycol aldehyde to bond to the hemoglobin at the Val-1($\beta$). In preferred embodiments of these methods, the polyalkylene glycol is a PEG, the Hb is hemoglobin A, and the borohydride is sodium cyano borohydride. Preferably, a second PEG aldehyde also bonds to the hemoglobin at a Val-1($\alpha$). In particularly preferred embodiments, at least 4 PEG aldehydes bond to the hemoglobin at free amino groups. In some embodiments, the polyalkylene glycol does not crosslink the hemoglobin intramolecularly or intermolecularly; in other embodiments, the polyalkylene glycol does crosslink the hemoglobin.

In additional embodiments, the present invention is directed to a method of producing a hemoglobin comprising a polyethylene glycol (PEG), wherein the PEG is covalently bonded to the hemoglobin at the $\alpha$-amino of a Val-1($\beta$). The method comprises incubating the hemoglobin with a PEG aldehyde and a borohydride under conditions and for a time sufficient for the PEG to bond to the hemoglobin at the Val-1($\beta$), wherein the PEG aldehyde has the formula wherein p is an integer from 2 to 6, q is 1 or 2, n is an integer from about 125 to about 500, and R is selected from the group consisting of OH, OCH$_3$, CH$_2$OH, CH$_2$OCH$_3$, CH$_2$CH$_2$OH, and CH$_2$CH$_2$OCH$_3$. Preferably, q is 1, n is about 125, and R is CH$_2$CH$_2$OCH$_3$.

In still other embodiments, the present invention is directed to a method of producing a hemoglobin comprising a polyethylene glycol (PEG), wherein the PEG is covalently bonded to the hemoglobin at the α-amino of a Val-1(β) and crosslinks the hemoglobin intramolecularly or intermolecularly. The method comprises incubating the hemoglobin with a PEG aldehyde and a borohydride under conditions and for a time sufficient for the PEG to bond to the hemoglobin at the Val-1(β), wherein the PEG aldehyde has the formula wherein each p is independently an integer from 2 to 6, each q is independently 1 or 2, and n is an integer from about 15 to about 250.

The present invention is additionally directed to a hemoglobin comprising a polyalkylene glycol, wherein the polyalkylene glycol is a polypropylene glycol or a polyethylene glycol (PEG), wherein the polyalkylene glycol is covalently bonded to the hemoglobin at a thiol moiety through a phenylsuccinimido linkage, and wherein no polyalkylene glycol is covalently bonded to a Cys-93(β). Preferably, the polyalkylene glycol is a PEG, and the hemoglobin is hemoglobin A. In these embodiments, the polyalkylene glycol can crosslink the hemoglobin or can decorate the hemoglobin.

In still other embodiments, the invention is directed to a hemoglobin comprising a polyethylene glycol (PEG), wherein the PEG is covalently bonded to the hemoglobin at a thiol moiety through a phenylsuccinimido linkage, and wherein no PEG is covalently bonded to a Cys-93(β). The hemoglobin has the formula wherein n is an integer from about 125 to about 500; m is an integer from about 2 to about 16; R is carbamate, urea, or amide; R' is carbamate, urea, amide, or oxygen; Y is 4-phenylsuccinimido or 3-phenylsuccinimido; and Y' is methyl or hydrogen. Preferably, the Hb is hemoglobin A, Y is 4-phenylsuccinimido, Y' is methyl, R is carbamate, R' is oxygen, n is about 125, and M is an integer from about 6 to about 8.

The invention is also directed to a hemoglobin comprising a polyethylene glycol (PEG), wherein the PEG is covalently bonded to the hemoglobin at a thiol moiety through a phenylsuccinimido linkage, and wherein no PEG is covalently bonded to a Cys-93(β), the hemoglobin having the formula wherein n is an integer from about 15 to about 250, R and R' are the same or different and are carbamate, urea, or amide, Y and Y' are the same or different and are 4-phenylsuccinimido or 3-phenylsuccinimido, and Hb and Hb' are the same or different hemoglobin molecule. Preferably, Y and Y' are both 4-phenylsuccinimido, and R and R' are both carbamate.

In still other embodiments, the invention is directed to a method for making a hemoglobin comprising a polyalkylene glycol, wherein the polyalkylene glycol is polypropylene glycol or polyethylene glycol (PEG), and wherein the polyalkylene glycol is covalently bonded to the hemoglobin at a thiol moiety through a phenylsuccinimido linkage. The method comprises (a) conjugating a reagent to a Cys-93(β) sulfhydryl group of the hemoglobin by a reversible method; (b) treating the hemoglobin with a maleidophenyl polyalkylene glycol and iminothiolane under conditions and for a time sufficient for the polyalkylene glycol to conjugate to the thiol moiety of the hemoglobin through a phenylsuccinimido linkage; and (c) removing the reagent from the Cys-93(β) sulfhydryl group of the hemoglobin. In preferred embodiments, the polyalkylene glycol is a PEG. The reagent can be an oxidized glutathione or, preferably, a dithiopyridine or a mixed disulfide of pyridine and polyalkylene glycol. A preferred mixed disulfide of pyridine and polyalkylene glycol is a mixed disulfide of pyridine and PEG-5000.

The present invention is additionally directed to a method for making a hemoglobin comprising a polyethylene glycol (PEG), wherein the PEG is covalently bonded to the hemoglobin at a thiol moiety through a phenylsuccinimido linkage. The method comprises (a) conjugating a reagent to a Cys-93(β) sulfhydryl group of the hemoglobin by a reversible method; (b) treating the hemoglobin with a maleidophenyl PEG and iminothiolane under conditions and for a time sufficient for the PEG to conjugate to the thiol moiety of the hemoglobin through a phenylsuccinimido linkage; and (c) removing the reagent from the Cys-93(β) sulfhydryl group of the hemoglobin, wherein the hemoglobin comprising the PEG has the formula wherein n is an integer from about 125 to about 500; m is an integer from about 2 to about 16; R is carbamate, urea, or amide; R' is carbamate, urea, amide, or oxygen; Y is 4-phenylsuccinimido or 3-phenylsuccinimido; and Y' is methyl or hydrogen. In preferred embodiments, the Hb is hemoglobin A, Y is 4-phenylsuccinimido, Y' is methyl, R is carbamate, R' is oxygen, n is about 200, and M is an integer from about 6 to about 8.

In still other embodiments, the present invention is directed to a method for making a hemoglobin comprising a polyethylene glycol (PEG), wherein the PEG is covalently bonded to the hemoglobin at a thiol moiety through a phenylsuccinimido linkage. The method comprises (a) conjugating a reagent to a Cys-93(β) sulfhydryl group of the hemoglobin by a reversible method; (b) treating the hemoglobin with a maleidophenyl PEG and iminothiolane under conditions and for a time sufficient for the PEG to conjugate to the thiol group of the hemoglobin through a phenylsuccinimido linkage; and (c) removing the reagent from the Cys-93(β) sulfhydryl group of the hemoglobin. The hemoglobin comprising the PEG has the formula wherein n is an integer from about 15 to about 250, R and R' are the same or different and are carbamate, urea, or amide, Y and Y' are the same or different and are 4-phenylsuccinimido or 3-phenylsuccinimido, and Hb and Hb' are the same or different hemoglobin molecule. Preferably, Y and Y' are both 4-phenylsuccinimido, and R and R' are both carbamate. Hb and Hb' can be the same or different hemoglobin A tetramers.

The invention is additionally directed to an improved PEGalated hemoglobin comprising a PEG covalently bonded to the hemoglobin at a thiol moiety through a phenylsuccinimido linkage. In these embodiments, the improvement comprises an absence of a PEG bonded to a Cys-93($\beta$). Preferably, the phenylsuccinimido linkage is a 4-phenylsuccinimido linkage.

In additional embodiments, the invention is directed to an improvement in a method for producing a PEGalated hemoglobin comprising PEG covalently bonded to the hemoglobin at a thiol moiety through a phenylsuccinimido linkage, where the method comprises treating the hemoglobin with a maleidophenyl PEG and iminothiolane under conditions and for a time sufficient for the PEG to conjugate to the thiol moiety of the hemoglobin through a phenylsuccinimido linkage. The improvement comprises conjugating a reagent to a Cys-93($\beta$) sulfhydryl group of the hemoglobin by a reversible method before treating the hemoglobin with the PEG, then removing the reagent after treating the hemoglobin with the PEG. The reagent can be oxidized glutathione or, preferably, dithiopyridine or a mixed disulfide of pyridine and a polyalkylene glycol. A preferred mixed disulfide of a pyridine and a polyalkylene glycol is a mixed disulfide of pyridine and PEG-5000.

The present invention is also directed to a hemoglobin comprising a PEG, produced by any of the methods described above. Additionally, any of the hemoglobin compositions provided above can be usefully provided in a pharmaceutically acceptable excipient, for use in therapeutic applications.

DETAILED DESCRIPTION OF THE INVENTION

The present invention is directed toward novel hemoglobin (Hb) compositions, and novel methods of preparing those compositions. The Hb compositions comprise hemoglobin molecules that are covalently bonded to polyalkylene (=polyoxy alkylene) glycols by methods that retain the functionality of the hemoglobin's Cys-93($\beta$) residues, which are important for maintaining a low oxygen affinity.

Three novel chemical methods are described for covalently bonding the polyalkylene glycol to the Hb, while avoiding the Cys-93($\beta$) residues. All three methods are directed to the production of Hbs bonded to polyalkylene glycols, where the bonding is at precise amino acid residues of the Hb. Additionally, all three methods can be adjusted to allow increasing or decreasing amounts of polyalkylene glycols to be bonded to the Hb, thus allowing the production of Hbs with as few as one or as many as 10 or more polyalkylene glycols attached. The first method employs carbodiimide to form an amide linkage with Hb carboxyl moieties; the second utilizes reductive alkylation chemistry to bond the polyalkylene glycol to amino residues of the Hb; and the third is an improvement of the previously developed thiolation mediated maleimide method that bonds the polyalkylene glycol to an Hb thiol moiety through phenylsuccinimido linkage, wherein the improvement avoids polyalkylene glycol bonding to the Cys-93($\beta$) thiol moiety.

Hemoglobin, or "Hb" is defined herein as (a) an iron-containing respiratory pigment found in vertebrate red blood cells that consists of globin composed of four subunits (a tetramer) each of which is linked to a heme molecule, that functions in oxygen transport to the tissues after conversion to oxygenated form in the gills or lungs, and that assists in carbon dioxide transport back to the gills or lungs after surrender of its oxygen; and (b) recombinantly produced hemoglobin; $\alpha\beta$-dimers of hemoglobin, inter- or intramolecularly crosslinked hemoglobin, as well as modified versions of the hemoglobins provided above, which include but are not limited to modifications increasing or decreasing the oxygen affinity of hemoglobin. All hemoglobins of the present invention are capable of binding heme and are comprised of at least an $\alpha\beta$-dimer. The hemoglobins of the present invention are preferably from mammals, and more preferably from human beings. In the most preferred embodiments, the hemoglobin is hemoglobin A (HbA).

As used herein, a polyalkylene glycol includes any compound of the formula X-[O—R]$_n$—Y, wherein R is an alkyl group, n is an integer from about 5 to about 1000, and X and Y can be anything. However, when the polyalkylene glycol is used in the methods of the present invention to produce the novel Hb-polyalkylene glycol compositions described herein, at least one of X or Y must comprise a functional group that is required in the method. For the amidation method, that functional group is an amino group; for the reductive alkylation method the functional group is an aldehyde; and for the improved thiolation mediated maleimide method, the functional group is 3- or 4-phenylmaleimido. The skilled artisan could, without undue experimentation, determine numerous X or Y constituents that would be useful for various applications of the present invention.

In preferred embodiments, R is $CH_2$—$CH_2$, wherein the polyalkylene glycol is a polyethylene glycol (PEG), or R is $CH_2$—$CH_2$—$CH_2$, wherein the polyalkylene glycol is polypropylene glycol. These polyalkylene glycols are preferred because they are readily commercially available. In the most preferred embodiments, the polyalkylene glycol is PEG, because PEG is commercially available in many forms (see, e.g., Shearwater Corporation (Huntsville, Ala.) catalog, at www.shearwatercorp.com. The PEGs or polypropylene glycols useful for the present invention do not need to have R groups that are completely $CH_2$—$CH_2$ or $CH_2$—$CH_2$—$CH_2$, respectively. The skilled artisan would understand that PEGs or polypropylene glycols useful for the present invention could have a substantial amount of substitutions in these R groups. Therefore, encompassed within the definition of PEG or polypropylene glycol are forms wherein the R groups are a majority of $CH_2$—$CH_2$ or $CH_2$—$CH_2CH_2$, respectively, and wherein the Hb-PEG or Hb-polypropylene glycol made using that PEG or polypropylene glycol according to the invention retains the same oxygen affinity and vasoactivity as the analogous Hb-PEG or Hb-polypropylene glycol having R groups that are exclusively $CH_2$—$CH_2$ or $CH_2$—$CH_2CH_2$, respectively.

The methods provided herein can be used for producing novel Hb-polyalkylene glycol compositions wherein the polyalkylene glycol decorates the Hb, as well as wherein the polyalkylene glycol crosslinks the Hb. As used herein, the term "decorate" or "surface decorate" refers to the characteristic of the Hb-polyalkylene glycol wherein the polyalkylene glycol is bonded to the Hb at only one point, usually at one end of the polyalkylene glycol, such that the polyalkylene glycol does not crosslink the Hb with itself or another Hb. By contrast, the term "crosslink" refers to the characteristic of the Hb-polyalkylene glycol wherein the polyalkylene glycol is bonded to an Hb at two points, usually at each end, such that the polyalkylene glycol links together two subunits of the same Hb ("intramolecular crosslink") or the polyalkylene glycol links together different Hb molecules ("intermolecular crosslink"). When more than one polyalkylene glycol is bonded to a Hb, there can be both intra- and intermolecular crosslinking.

As is generally known in the art, polyalkylene glycols of various sizes can be utilized to decorate or crosslink Hb. For decoration, preferred sizes are polyalkylene glycols of 5,000–20,000 daltons, which is equivalent to about 125 to about 500 —O—$CH_2$—$CH_2$ units when the polyalkylene glycol is PEG, although other sizes can be useful. For intramolecular crosslinking, polyalkylene glycols of 600–5000 daltons (equivalent to a PEG with about 15–125 —O—$CH_2$—$CH_2$— units) are particularly useful; for intermolecular crosslinking, polyalkylene glycols of 600–10,000 daltons (equivalent to a PEG with about 15–250 —O—$CH_2$—$CH_2$— units) are particularly useful.

As discussed in Example 4, the inventors have further discovered an unexpected useful property of the polyalkylene glycol-modified hemoglobins of the present invention, particularly those where the polyalkylene glycol is used to surface decorate the hemoglobin. The inventors have discovered that the modified hemoglobins have an increased hydrodynamic volume that has an apparent molecular weight, when measured by molecular sieve chromatography, that is much greater than its true molecular weight. Where the polyalkylene glycol is used to surface decorate the hemoglobin, the increased volume reflects a size of hemoglobin that is nearly six times the molecular mass of the polyalkylene glycol that is bonded to it. This increased hydrodynamic size is known to be advantageous.

I. Production of Hb-polyalkylene Glycols by Amidation.

Figure 1:
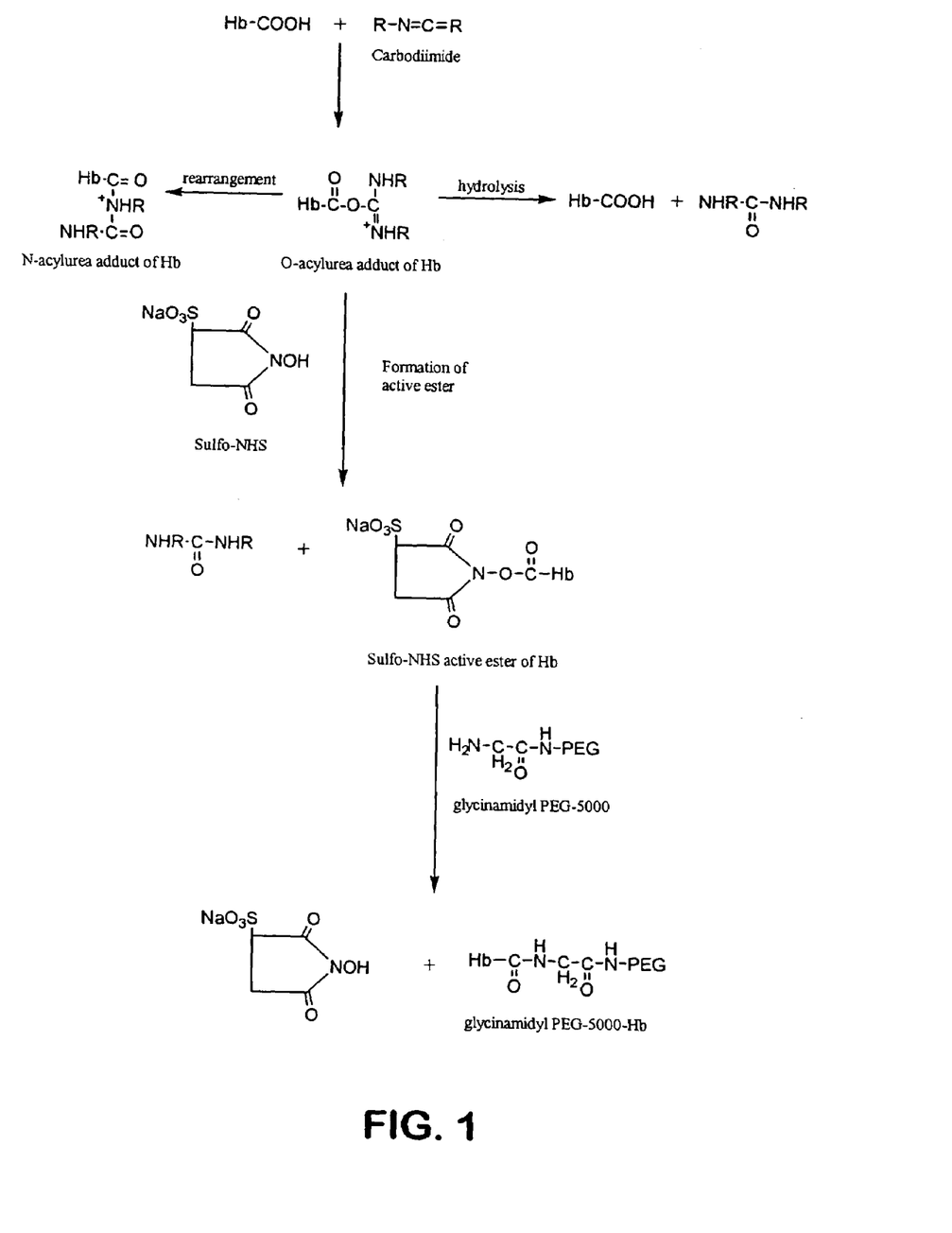
FIG. 1 is a schematic representation of the amidation of carboxyl groups of HbA in the presence of EDC, Sulfo-NHS, and glycinamidyl PEG-5000.

The inventors disclose herein the discovery that various nucleophilic polyalkylene glycol molecules that have a free terminal amine with a $pK_a$ below about 9.0 can be bonded to basic carboxyl moieties of Hb through modifications of an amidation procedure that has been previously developed (Rao and Acharya, 1994). However, because the previously disclosed amidation procedure was developed for attaching only very small molecules to Hb, the skilled artisan would understand that, without the instant disclosure, the amidation procedure would not necessarily be useful for attaching the relatively large polyalkylene glycol molecules to Hb. The methods comprise mixing, in a suitable buffer, the hemoglobin, the polyalkylene glycol and a carbodiimide. In preferred embodiments, the carbodiimide is 1-ethyl-3-(3'-dimethylaminopropyl)carbodiimide (EDC), and the mixture also comprises N-hydroxysulfosuccinimide (FIG. 1). The N-hydroxysulfosuccinimide increases the efficiency of the reaction by "trapping" the carbodiimide-activated carboxyl group of the Hb (Id.).

In these methods, if a relatively low carbodiimide concentration is utilized in the mixture (i.e., about 10 mM), the methods result in bonding of the polyalkylene glycol at the Hb Glu-43(β) residues. With increasing carbodiimide concentrations (i.e., up to 50 mM or more), bonding also occurs at the Glu-22(β) position, then at the Asp-47(β) position. Bonding can also occur at the terminal carboxyl position (the α-carboxyl groups of Arg-141(α) and/or His-146(β)), or at other carboxyl residues, albeit with greater difficulty, requiring higher carbodiimide concentrations, a higher ratio of polyalkylene glycol:Hb, and/or a longer incubation time. Thus, by varying the reaction conditions using routine experimentation, varying amounts of the polyalkylene glycol can be attached to the Hb, up to 10 or more polyalkylene glycols on an HbA tetramer. In preferred embodiments where the polyalkylene glycol is used for decorating the hemoglobin, the resulting Hb is an HbA with about 6–8 polyalkylene glycols, wherein the polyalkylene glycols are PEG-5000 (having about 125 —O—$CH_2$—$CH_2$ units).

Figure 2:
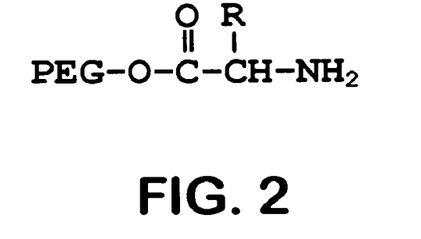
FIG. 2 is the structure of the amino acid ester of PEG.

The skilled artisan could identify, without undue experimentation, numerous nucleophilic polyalkylene glycols having a terminal amine with a $pK_a$ below 9 that are useful for the present invention. Useful examples are amino acid esters of PEG (FIG. 2), particularly where R=H (glycine ester) or $CH_2$—$COO^-$ (aspartic acid ester). For decoration, the nucleophilic polyalkylene glycol should have only one reactive terminal amine; for crosslinking, there should be two terminal amines, preferably at each end of the polyalkylene glycol molecule. In preferred embodiments, the polyalkylene glycol for decoration is a PEG with the formula wherein n is an integer from about 125 to about 500, W is NH or O, R is an amino acid side chain, and R' is selected from the group consisting of OH, $OCH_3$, $CH_2OH$, $CH_2OCH_3$, $CH_2CH_2OH$, and $CH_2CH_2OCH_3$. R can be any amino acid side chain, including those of amino acids that are not used in proteins. In preferred embodiments, R is H or $CH_2COO^-$ (side chain of aspartic acid). The aspartic acid side chain is useful in applications where it is desired that the net charge of the modified Hb residue is retained. As has been previously determined, the retention of the charge on the Glu-43(β) residue is important for retaining a low oxygen affinity of the modified Hb (Rao and Acharya, 1994).

In the above formula, W is preferably NH, which creates a good nucleophile for the PEGalation reaction. The glycinamidyl PEG thus described can be produced by acetylation of PEG amine with glycine. See Example 2 (see also Example 1 for a method of making an analogous bifunctional glycinamidyl PEG useful as a crosslinking reagent, as described below).

The CHR in the above formula can also be usefully substituted with NH, providing a PEG hydrazide. This reagent can be generated by reacting carboxymethylated PEG with hydrazine by known methods.

For inter- or intramolecular crosslinking, the preferred formula for the nucleophilic polyalkylene glycol is H$_2$N—CHR—CO—W—CH$_2$—CH$_2$—[O—CH$_2$—CH$_2$]$_n$—NH—CO—W'—CHR'—NH$_2$ wherein n is an integer from about 15 to about 125 where intramolecular crosslinking is desired, and 15–250 for intermolecular crosslinking, W and W' are each independently NH or O, and R and R' are each independently an amino acid side chain. As with the preferred PEG for decoration described above, R can be any amino acid side chain, including those of amino acids that are not used in proteins, but in preferred embodiments, R is H or CH$_2$COO$^-$; the CHR of CHR' can be substituted for NH; and W is preferably NH.

The amidation reaction can be performed for about 15 min. to about 3 hours, preferably for about 1 hour at room temperature. The amidation reaction may also be carried out at about 4° C. overnight if desired. The pH of the amidation reaction is preferably from about 5.8 to about 7.5. In a preferred embodiment, the amidation reaction is carried out at a pH of about 7 resulting in amidation predominately at the Glu-43(β) carboxyl group of hemoglobin. The reaction can be performed in 0.1 M KCl buffer at the desired pH (6–8) using a pH-stat, to keep the pH of the reaction mixture constant with HCl, since the amidation reaction raises the pH (Rao and Acharya, 1994). However, it is preferred that the reaction takes place in MES buffer, preferably at about 20 mM, since that procedure is easier than using a pH-stat. In preferred embodiments, the molar ratio of PEG to Hb in the amidation reaction is about 50. Oxy Hb is the preferred conformational state of the protein since it makes the execution of the amidation reaction protocol simpler relative to that using deoxy Hb. See Example 3 for typical reaction conditions.

Figure 3:
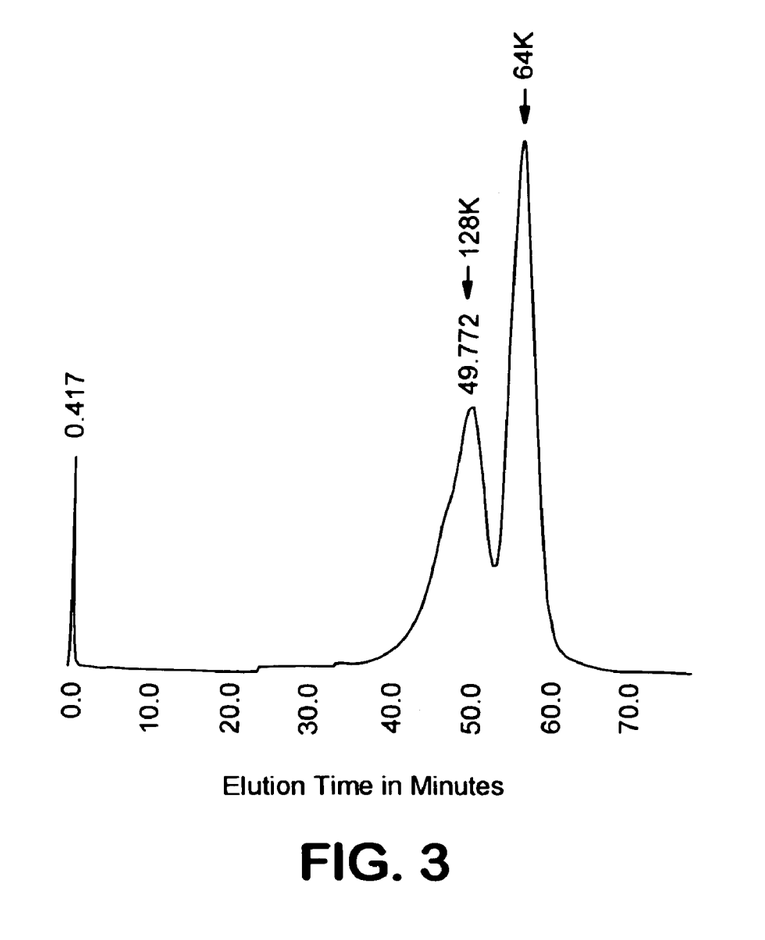
FIG. 3 is a graph representing the elution profile of size exclusion chromatography of HbA amidated with the glycine ester of PEG-5000 in the present of 10 mM EDC for 1 hour at pH 7.0 and room temperature. After the reaction, the sample was first gel filtered on a G-25 column to remove the excess reagents. The peak marked 64 K represents HbA, and the peak migrating to the 128 K marker represents HbA PEGalated at Glu-43($\beta$).

After the reaction, the Hb-polyalkylene glycol is preferably separated from the unreacted reagents by molecular sieve chromatography, for example using Sephadex® G-25 or Superose®12, preferably in a neutral buffer such as 10 mM phosphate buffered saline, pH 7.4. A typical elution pattern is provided in FIG. 3.

The amidation methods described above create novel Hb-polyalkylene glycol compositions. Thus, in some embodiments, the present invention provides a hemoglobin comprising a polyalkylene glycol, wherein the polyalkylene glycol is covalently bonded to the hemoglobin with an amide linkage at a Glu-43(β). Preferably, the polyalkylene glycol is a polypropylene glycol or a PEG, most preferably a PEG. In preferred embodiments, the Hb is HbA. It is also preferred that the Hb also comprises a second PEG that is covalently bonded to a Glu-22(β) with an amide linkage.

In some aspects of these embodiments, the polyalkylene glycol does not crosslink the Hb either intramolecularly or intermolecularly. Preferably, the polyalkylene glycol has the formula Hb-(CO—NH—CHR—CO—W—CH$_2$—CH$_2$—[O—CH$_2$—CH$_2$]$_n$—R')$_m$ wherein n is an integer from about 125 to about 500, m is an integer from 1 to 10, W is NH or O, R is an amino acid side chain, R' is selected from the group consisting of OH, OCH$_3$, CH$_2$OH, CH$_2$OCH$_3$, CH$_2$CH$_2$OH, and CH$_2$CH$_2$OCH$_3$, and wherein at least one PEG is bonded to the Hb at Glu-43(β). In the most preferred embodiments, the Hb is a hemoglobin A, W is NH, n is about 125, m is 6–8, R is H or CH$_2$COOH, and R' is CH$_2$CH$_2$OCH$_3$.

In other aspects of these embodiments, the polyalkylene glycol inter- or intramolecularly crosslinks the Hb. In these aspects, the Hb-polyalkylene glycol preferably has the formula Hb-CO—NH—CHR—CO—W—CH$_2$—CH$_2$—[O—CH$_2$—CH$_2$]$_n$—NH—CO—W'—CHR—NH—CO—Hb' wherein Hb and Hb' are the same or different hemoglobin molecule, n is an integer from about 15 to about 250, W and W' are each independently NH or O, R is an amino acid side chain, and HbA and/or HbA' is bonded to the PEG with an amide linkage at Glu-43(β). In the most preferred embodiments, R is H or CH$_2$COOH, Hb and Hb' are different hemoglobin A tetramers, W and W' are both NH, and the PEG intermolecularly crosslinks HbA with HbA'.

II. Production of Hb-polyalkylene Glycols by Reductive Alkylation.

It has further been discovered that polyalkylene glycol can be covalently bonded to Hb through reductive alkylation targeted to the α-amino groups of HbA, present at Val-1(α) and Val-1(β). Like the amidation method described above, reductive alkylation has also been previously used to bond small compounds to Hb (Acharya et al., 1983; Acharya and Sussman, 1984; Acharya et al., 1991). However, the utility of applying this method to polyalkylene glycol linkage to Hb would not be obvious to the skilled artisan because the polyalkylene glycols utilized in the present invention are much larger than the compounds previously linked to Hb using reductive alkylation.

The reactivity of the amino groups of a protein for reductive alkylation is a direct correlate of their propensity to generate Schiff base adducts with the carbonyl reagents. In the absence of any accessibility problems, the propensity of an amino groups to form Schiff base adducts is dictated by their pKa values and the pH of the reaction mixture, since Schiff-base adduct formation requires the unprotonated form of amino groups. In proteins, the pKa of the α-amino groups is around neutral pH and is lower than those of the ε-amino groups. This feature of the α-amino groups of proteins facilitates the selective reductive alkylation of the α-amino groups of proteins around neutral pH, as far as the α-amino groups are accessible to the solvent phase for the formation Schiff base adduct and a limiting concentration of carbonyl reagent (aldehyde) is used. In Hb, a tetrameric protein, there are four α-amino groups per tetramer (for a molecular size of 64,000 Dalton) and all four α-amino groups are accessible for reductive alkylation with simple aliphatic aldehydes. A discrimination between the α-amino group of the α-chains [Val-1(α)] and that of the β-chains [Val-1(β)] of Hb can be achieved by modulating the pH of the reaction medium and the amount of the carbonyl reagent present during reductive alkylation (Acharya et al., 1983). A choice of lower pH (around 6.5) and a carbonyl reagent concentration that is just about 2 to 3 fold molar excess over that of Hb tetramer, results in targeting the reductive alkylation of Hb predominantly to the Val-1(β) residues of Hb. With simple aliphatic aldehydes, a slightly higher excess of the reagent, about 5 fold molar excess over the Hb tetramer, and a pH around 7.4 results in the modification of α-amino groups of Val-1(α) of Hb besides Val-1(β). Additional reductive alkylations at the ε-amino groups of Hb requires much higher concentrations of the reagent (Acharya et al., 1991).

An advantage of the reductive alkylation chemistry for modification of Hb, particularly when targeted to Hb α-amino groups, is that the modification of Hb at its α-amino groups does not increase the oxygen affinity of HbA (Acharya and Sussman, 1984, as established with low molecular weight neutral aldehydes). In fact, the modification of all four α-amino groups of HbA by reductive alkylation by neutral aliphatic aldehydes results in a slight reduction in the oxygen affinity of HbA.

Figure 6:
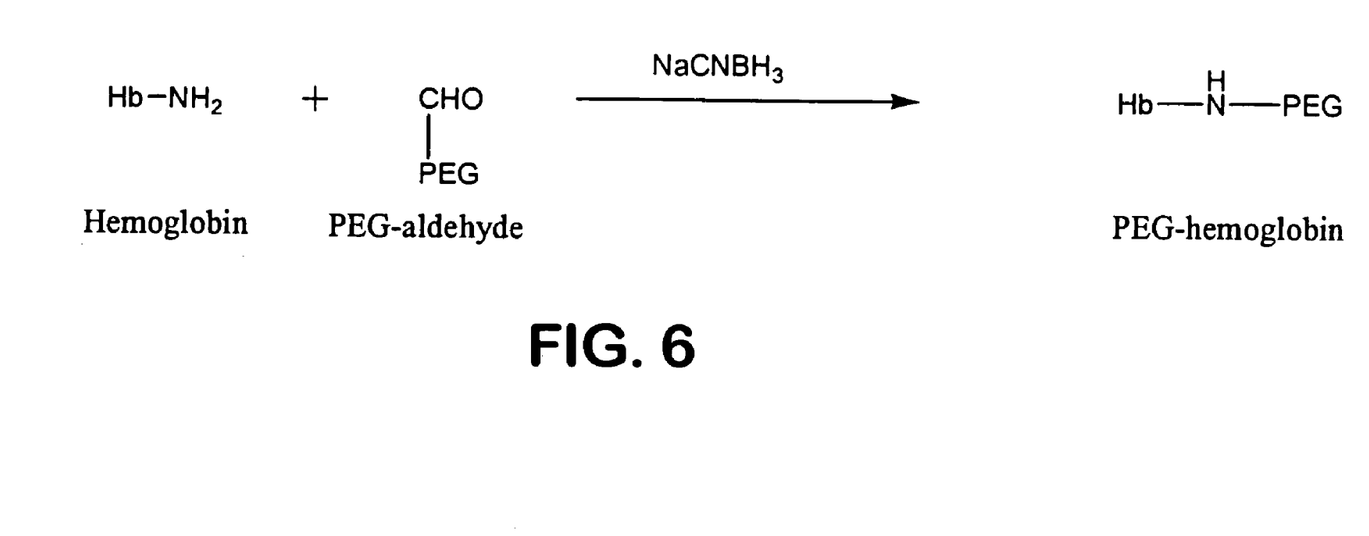
FIG. 6 is a schematic representation of reductive alkylation of amino groups of Hb using PEG-aldehyde.

As adopted for linkage of polyalkylene glycols to Hb, the method of the present invention comprises incubating the hemoglobin with a polyalkylene glycol aldehyde and a borohydride under conditions and for a time sufficient for the polyalkylene glycol aldehyde to bond to the hemoglobin at the Val-1(β). In preferred embodiments, the polyalkylene glycol is a PEG, the Hb is a hemoglobin A, and the borohydride is sodium cyano borohydride (FIG. 6). Although the reaction can be performed with deoxy Hb, the oxy form is preferred since handling Hb under oxy conditions is simpler.

The reductive alkylation reaction is preferably performed for about 15 min. to about 3 hours, and more preferably for about 1 hour, at room temperature. The reductive alkylation reaction can also be carried out at about 4° C. overnight if desired. A preferred buffer for the reaction is 10 mM phosphate buffer, containing 150 mM NaCl. However, the use of Tris or Bis-Tris buffer increases the propensity of the reaction to occur at Val-1(β) rather than Val-1(α). The molar ratio of polyalkylene glycol aldehyde to Hb in the reaction is preferably from about 2:1 to about 40:1. To achieve linkage of a greater number of polyalkylene glycol aldehydes to the hemoglobin (i.e., as many as 6 to 8 polyalkylene glycol aldehyde molecules) the polyalkylene glycol aldehyde:Hb molar ratio should be about 20:1 to about 40:1, and, preferably, a slightly higher pH (8.0 to 8.5). Conversely, to achieve linkage at only one or two sites, i.e., the Val-1(β) residues, the reaction is carried out at a pH of from about 6 to about 7, preferably at about 6.5 in Bis-Tris buffer, and at a polyalkylene glycol aldehyde:Hb molar ratio of from about 2:1 to about 6:1, preferably from about 2:1 to about 3:1.

In another embodiment of this aspect of the invention, polyalkylene glycol molecules can be attached at predominately the Val-1(α) residues of HbA by performing the reductive alkylation method described above at a pH of from about 7 to about 8, preferably 7.4, and at a PEG to HbA molar ratio of from about 2:1 to about 10:1, preferably 5:1. The process of attaching PEG to the Val-1(α) residues of HbA is preferably carried out in the presence of inosine hexaphosphate (IHP), which blocks the residues of the ββ cleft (Val-1(β)) for reaction.

In still another embodiment of this aspect of the invention, polyalkylene glycol molecules can be attached to Hb at substantially all α-amino groups and lysine residue ε amino groups with low pKa values by the reductive alkylation method described above, by performing the reaction at a pH of about 7.4 to 8.5, and at a temperature of about 37° C., and using a high molar ratio of polyalkylene glycol aldehyde:Hb (~40:1).

After the reaction, the Hb-polyalkylene glycol is preferably separated from the unreacted reagents by molecular sieve chromatography, as described for the results of the amidation methods.

Figure 7:
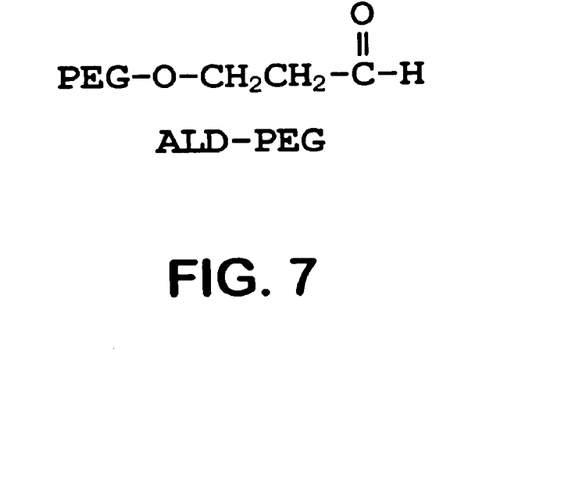
FIG. 7 shows the structure of PEG-propionaldehyde for surface decoration of HbA targeted to $\alpha$-amino groups of HbA.

The skilled artisan can design, without undue experimentation, a wide range of polyalkylene glycol aldehydes useful for modification of Hb by reductive alkylation. A preferred form is PEG-propionaldehyde (FIG. 7). The skilled artisan would understand that with one propionaldehyde moiety, this reagent would be useful for decoration of Hb; with two propionaldehyde moieties (preferably at each end), the reagent would be useful for crosslinking applications.

Another preferred polyalkylene glycol aldehyde for decoration is wherein p is an integer from 2 to 6, q is 1 or 2, n is an integer from about 125 to about 500, and R is selected from the group consisting of OH, OCH$_3$, CH$_2$OH, CH$_2$OCH$_3$, CH$_2$CH$_2$OH, and CH$_2$CH$_2$OCH$_3$. Preferably, q is 1, n is about 125, and R is CH$_2$CH$_2$OCH$_3$.

For crosslinking, a preferred polyalkylene glycol aldehyde form is wherein each p is independently an integer from 2 to 6, each q is independently 1 or 2, and n is an integer from about 15 to about 250.

The reductive alkylation methods thus described are useful for the creation of novel Hb-polyalkylene glycol compositions. Thus, in some embodiments, the present invention provides a hemoglobin comprising a polyalkylene glycol, and wherein the polyalkylene glycol is covalently bonded to the hemoglobin at the α-amino of a Val-1(β). Preferably, the polyalkylene glycol is a polypropylene glycol or a PEG, most preferably a PEG. In preferred embodiments, the Hb is HbA. It is also preferred that the Hb also comprises a second PEG that is covalently bonded to the hemoglobin at the α-amino of a Val-1(α).

In some embodiments, the polyalkylene glycol does not crosslink the Hb intramolecularly or intermolecularly. In those embodiments, a preferred Hb-polyalkylene glycol composition is wherein p is an integer from 2 to 6, q is 1 or 2, n is an integer from about 125 to about 500, m is an integer from 1 to 10, and R is selected from the group consisting of OH, OCH$_3$, CH$_2$OH, CH$_2$OCH$_3$, CH$_2$CH$_2$OH, and CH$_2$CH$_2$OCH$_3$. In the most preferred embodiments, q is 1, n is about 125, m is 1–4, and R is CH$_2$CH$_2$OCH$_3$.

In other embodiments, the polyalkylene glycol does crosslink the Hb intramolecularly or intermolecularly. In those embodiments, a preferred Hb-polyalkylene glycol composition is wherein Hb and Hb' are the same or different hemoglobin molecule, each p is independently an integer from 2 to 6, each q is 1 or 2, preferably 1, and n is an integer from about 15 to about 250. In intramolecular crosslinking embodiments, it is preferred that Hb and Hb' are the same hemoglobin A tetramer. In intermolecular crosslinking embodiments, it is preferred that Hb and Hb' are different hemoglobin A tetramers.

III. Improvements in the Production of Hb-polyalkylene glycols by thiolation mediated maleimide chemistry An improvement has been developed for the previously discovered polyalkylene glycol-Hb linking method where Hb is incubated with iminothiolane and a maleidophenyl polyalkylene glycol, to form an Hb with a polyalkylene glycol linked to a Hb thiol group through a phenylsuccinimido linkage (first disclosed in U.S. patent application Ser. No. 425,137, which became U.S. Pat. No. 5,585,484).

As is well known, modification of the Cys-93($\beta$) residue of hemoglobin increases the oxygen affinity of Hb. Thus, if the oxygen affinity of the surface decorated Hb is critical for a given therapeutic application of acellular Hb, it may be advantageous to leave the Cys-93($\beta$) intact. This can be achieved by, for example, utilizing the amidation or reductive alkylation procedures described above. However, if one utilized the prior art to employ the thiolation-mediated maleimide method described in U.S. Pat. No. 5,585,484, there was no way to avoid the modification of the Cys-93($\beta$) residue. The present invention describes an improvement in that method that results in a polyalkylene glycol-modified Hb wherein the Cys-93($\beta$) residue is not modified. To that end, two procedures have been developed for preserving the Cys-93($\beta$) in the final product: (i) reversible blocking of the sulfhydryl group of Cys-93($\beta$) as mixed disulfide with glutathione and (ii) reversible blocking of the sulfhydryl group of Cys-93($\beta$) with a dithiopyridine or a mixed disulfide of pyridine and polyalkylene glycol.

Thus, the present invention provides a method for making a hemoglobin comprising a polyalkylene glycol, wherein the polyalkylene glycol is bonded to the hemoglobin at a thiol moiety through a phenylsuccinimido linkage. The method comprises (a) conjugating a reagent to a Cys-93($\beta$) sulfhydryl group of the hemoglobin by a reversible method; (b) treating the hemoglobin with a maleidophenyl polyalkylene glycol and iminothiolane under conditions and for a time sufficient for the polyalkylene glycol to conjugate to a hemoglobin thiol moiety through a phenylsuccinimido linkage; and (c) removing the reagent from the Cys-93($\beta$) sulfhydryl group of the hemoglobin. Step (b) is fully described in U.S. Pat. No. 5,585,484.

In these methods, the reagent is either glutathione or, preferably, dithiopyridine (for example by the method described in Example 5) or a mixed disulfide of pyridine and polyalkylene glycol. The pyridyl polyalkylene glycol mixed disulfide is preferred over glutathione because it is much easier to monitor the attachment of the large polyalkylene glycol than the glutathione. This monitoring is preferably performed by molecular sieve chromatography (e.g., with a Superose® 12 column), when the mixed disulfide of Hb and the polyalkylene glycol can be detected by an acceleration in the elution of the hemoglobin due to the increased hydrodynamic volume (a hemoglobin tetramer of 64,000 molecular weight with a PEG-5000 attached behaves like a protein having a molecular weight of 128,000). This chromatographic procedure will also conveniently separate the modified Hb from the unmodified Hb (or dithiopyridine) if the modification is not quantitative. By contrast, the formation of the mixed disulfide of Hb with glutathione is monitored with isoelectric focusing. Column chromatography must also still be performed with the glutathione procedure to remove the unreacted glutathione. If monitoring of the reaction is not necessary, then dithiopyridine is the preferred reagent because it provides for a cost effective, convenient method.

The mixed disulfide of pyridine and polyalkylene glycol is preferably a polypropylene glycol or a PEG, more preferably a PEG. The polyalkylene glycol of the mixed disulfide can be any convenient size, but preferably at least about 5000 molecular weight (about 125 O—CH$_2$—CH$_2$ units for a the pyridine-PEG mixed disulfide), since the attachment of a polyalkylene glycol of that size to Hb can be easily detected as a hydrodynamic volume change.

In these methods, the maleidophenyl polyalkylene glycol is preferably either a 4-phenylmaleimido polyalkylene glycol or a 3-phenylmaleimido polyalkylene glycol, most preferably a 4-phenylmaleimido polyalkylene glycol. The polyalkylene glycol is preferably either a polypropylene glycol or a PEG, most preferably a PEG.

For decoration, a preferred phenylmaleimido polyalkylene glycol is wherein n is an integer from about 125 to about 500; R is carbamate, urea, or amide; R' is carbamate, urea, amide, or oxygen; Y is 4-phenylmaleimido or 3-phenylmaleimido; and Y' is methyl or hydrogen. More preferably, Y is 4-phenylmaleimido, Y' is methyl, R is carbamate, R' is oxygen, and n is about 125.

For crosslinking, a preferred phenylmaleimido polyalkylene glycol is wherein n is an integer from about 15 to about 250, R and R' are the same or different and are carbamate, urea, or amide, and Y and Y' are the same or different and are 4-phenylmaleimido or 3-phenylmaleimido. More preferably, Y and Y' are both 4-phenylmaleimido, and R and R' are both carbamate.

This method thus provides novel modified hemoglobins. In some embodiments, the method provides a hemoglobin comprising a polyalkylene glycol, wherein the polyalkylene glycol is covalently bonded to the hemoglobin at a thiol moiety through a phenylsuccinimido linkage, and wherein no polyalkylene glycol is covalently bonded to a Cys-93($\beta$). Preferably, the polyalkylene glycol is a polypropylene glycol or a polyethylene glycol (PEG), most preferably a PEG. The hemoglobin is most preferably a hemoglobin A.

The polyalkylene glycol can decorate or crosslink the hemoglobin. A preferred decorated hemoglobin has the formula wherein n is an integer from about 125 to about 500; m is an integer from about 2 to about 16; R is carbamate, urea, or amide; R' is carbamate, urea, amide, or oxygen; Y is 4-phenylsuccinimido or 3-phenylsuccinimido; and Y' is methyl or hydrogen. In more preferred embodiments, the Hb is hemoglobin A, Y is 4-phenylsuccinimido, Y' is methyl, R is carbamate, R' is oxygen, n is about 200, and M is an integer from about 6 to about 8.

A preferred crosslinked hemoglobin has the formula wherein n is an integer from about 20 to about 500, R and R' are the same or different and are carbamate, urea, or amide, Y and Y' are the same or different and are 4-phenyl succinimido or 3-phenylsuccinimido, and Hb and Hb' are the same or different hemoglobin molecule. In the more preferred intramolecularly crosslinked Hb embodiments, Hb and Hb' are the same hemoglobin A tetramer, Y and Y' are both 4-phenylsuccinimido, and R and R' are both carbamate. In the more preferred intermolecularly crosslinked Hb embodiments, the Hb and Hb' are different hemoglobin A tetramers, Y and Y' are both 4-phenylsuccinimido, and R and R' are both carbamate.

The present invention also provides pharmaceutical compositions comprising any of the compositions described above and a pharmaceutically acceptable excipient. Suitable carriers include but are not limited to various physiologically acceptable solutions known in the art such as saline solution, Ringer's solution, lactated Ringer's solution, Locke-Ringer's solution, Kreb's Ringer's solution, Hartmann's balanced saline solution, and heparinized sodium citrate acid dextrose solution. The pharmaceutical compositions also may comprise known plasma substitutes and plasma expanders. The pharmaceutical compositions of the present invention may be used as blood substitutes, and the like, and may be administered by conventional means including but not limited to transfusion and injection.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples.

EXAMPLE 1

Preparation of Bifunctional Glycinamidyl PEG

5 Grams of O,O'(2-amino propyl) polyethylene glycol 600 (diamino PEG-600) was acylated with about two molar equivalents of BOC (tertiary butyloxy carbonyl)Glycyl-ONSu (N-hydroxy succinmidyl ester of t-butyloxy Glycine) in dry tetrahydrofuran at room temperature. After 16 hours, the analytical TLC showed trace amounts of unreacted amino compound. The solvent was evaporated under reduced pressure, and the residual oil is treated with trifluoroacetic acid:dichloromethane (TFA:DCM) at a 1:1 ratio by volume. The dry product was dried under vacuum over sodium hydroxide pellets and 4.5 grams of bifunctional glycinamidyl PEG was recovered.

EXAMPLE 2

Preparation of Monofunctional Glycinamidyl PEG

5 Grams of omega methoxy monoamine PEG was acylated with about one molar equivalent of N-hydroxy succinimidyl ester of t-butyloxy glycine in dry tetrahydrofuran at room temperature. After 16 hours, the analytical TLC showed trace amounts of unreacted amino compound. The solvent was evaporated under reduced pressure, and the residual oil is treated with trifluoroacetic acid:dichloromethane (TFA:DCM) at a 1:1 ratio by volume. The dry product was dried under vacuum over sodium hydroxide pellets and 4.8 grams of monofunctional glycinamidyl PEG was recovered.

EXAMPLE 3

Preparation of Hemoglobin A Decorated with Glycinamidyl PEG-5000.

A 2.0 mM solution of hemoglobin A (HbA) (in the oxy state) is dialyzed overnight at 4° C. against 20 mM MES buffer, pH 6.0. A 50 mM solution of glycinamidyl PEG-5000, and a 20 mM solution of N-hydroxysulfosuccinimide, both in MES buffer at pH 6.0 is also prepared. The HbA, glycinamidyl PEG-5000, and N-hydroxysulfosuccinimide solutions are mixed together to final concentrations of 0.5 mM HbA, 25 mM glycinamidyl PEG-5000, and 5 mM N-hydroxysulfosuccinimide. The reaction is initiated by the addition of 1-ethyl-3(3'-dimethylaminopropyl)carbodiimide (EDC) from a stock solution to a final concentration of 20 mM. The concentration of EDC stock solution is such that the volume of the solution added to initiate the amidation reaction is less than 2% of the total reaction volume. After addition of EDC, the reaction mixture is incubated at room temperature for 1 hr. The PEGalated HbA is separated from any non-PEGalated HbA by gel filtration on a Superose®-12 column with 10 mM phosphate buffered saline, pH 7.4.

EXAMPLE 4

Characterization of PEGalated Surface Decorated Hemoglobin

Amidation of HbA using 10 mM carbodiimide and glycyl ester of PEG-5000 as the nucleophile (an established reaction condition to site selectively activate the γ-carboxyl group of Glu-43(β)) generated a surface decorated product (FIG. 3) that exhibits a hydrodynamic volume comparable to that of HbA carrying two copies of PEG-5000 chain on Cys-93(β), as produced using the thiolation-mediated maleimide method of U.S. Pat. No. 5,585,484. Therefore, the apparent molecular size of Hb surface decorated with PEG-5000 appears to be dictated by the molecular size of the PEG chains rather than the chemistry used to link the PEG chains to Hb.

To increase the number of PEG-chains introduced on to Hb through side chain carboxylates, the surface decoration has been carried out in the presence of 50 mM carbodiimide (a condition known to activate all three high pKa carboxyl groups of Hb). A product with much higher apparent molecular size and very little of lower molecular size forms of HbA, was generated reflecting the conjugation of the PEG at side chain carboxyl groups other than that of Glu-43(β). The apparent molecular size of this product corresponded to that of the surface decorated sample of Hb generated by introducing 6 to 8 PEG-chains per tetramer by the thiolation mediated, maleimide chemistry based PEGalation reaction. Since both samples contain on an average six to eight PEG-5000 chains per tetramer, the results further support the conclusion that the hydrodynamic volume of surface decorated HbA depends primarily on the number of PEG-5000 chains placed on the Hb tetramer and is independent of the site of attachment and the chemistry used for attaching the PEG-chains.

The molecular sieve chromatographic patterns of HbA surface decorated with glycine ester of PEG-5000 using 25 mM EDC, revealed that the apparent molecular size of the major product of the reaction is intermediate to that of HbA with two equivalents of glycine ethyl ester of PEG-5000 and that of the sample containing on an average six to eight equivalents of glycine ethyl ester of PEG-5000.

Figure 4:
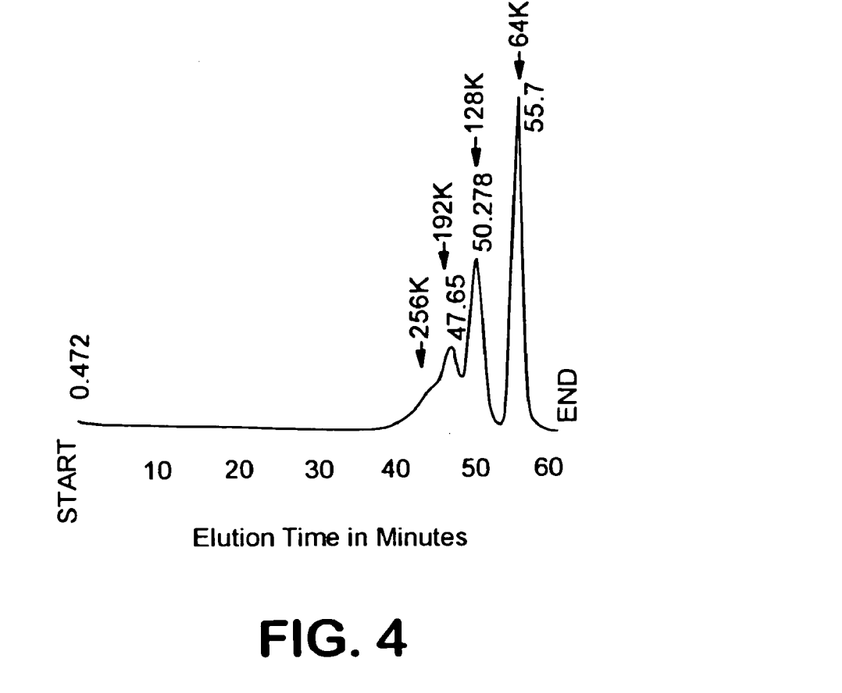
FIG. 4 is a graph representing the elution profile of XL-fumaryl-Lys-99-$\alpha\alpha$ HbA intermolecularly crosslinked with bis-maleidophenyl PEG-600. Each new component eluting earlier than crosslinked HbA present in the crosslinked sample represents the elution changes associated with an increase in the molecular size corresponding to 64,000 daltons.

In an attempt to correlate the apparent increase in the molecular size of HbA as consequence of PEGalation, the Superose®-12 column was calibrated by running a sample of intramolecularly crosslinked HbA (αα fumaryl HbA) intertetramerically crosslinked with bis-maleidophenyl PEG-600. HbA intramolecularly crossbridged within the central cavity between Lys-99(α) and Lys-99(α) using dibromosalicyl fumarate (XL fumaryl αα HbA) was intermolecularly crosslinked with bis-maleidophenyl PEG-600 to introduce intertetrameric crossbridged HbA. This sample containing intertetramerically crossbridged higher molecular weight forms of XL-fumaryl-αα HbA served as the markers for the elution position of multimeric forms of HbA. (FIG. 4). Each peak position eluting earlier to the intermolecularly crossbridged HbA corresponds to the next higher polymeric state of inter molecularly crossbridged HbA (FIG. 4). An elution position of 56 minutes on this column represents the molecular size of tetrameric Hb, with an apparent molecular weight of 64,000. Thus, the elution position of 50 minutes on the Superose®-12 column corresponds to that of octameric form with an apparent molecular weight of 128,000 daltons, the elution position around 47 minutes correspond to that of dodecameric protein with a molecular weight of 192,000 daltons, and the elution position of 44 minutes corresponds to that of a hexadecameric species, with an apparent molecular size of 256,000 daltons. The elution position of the main component of the sample generated by the amidation reaction using 50 mM EDC corresponds to that of hexadecameric (16 subunits, molecular size 256,000 Dalton) form of intra molecularly cross bridged HbA.

Figure 5:
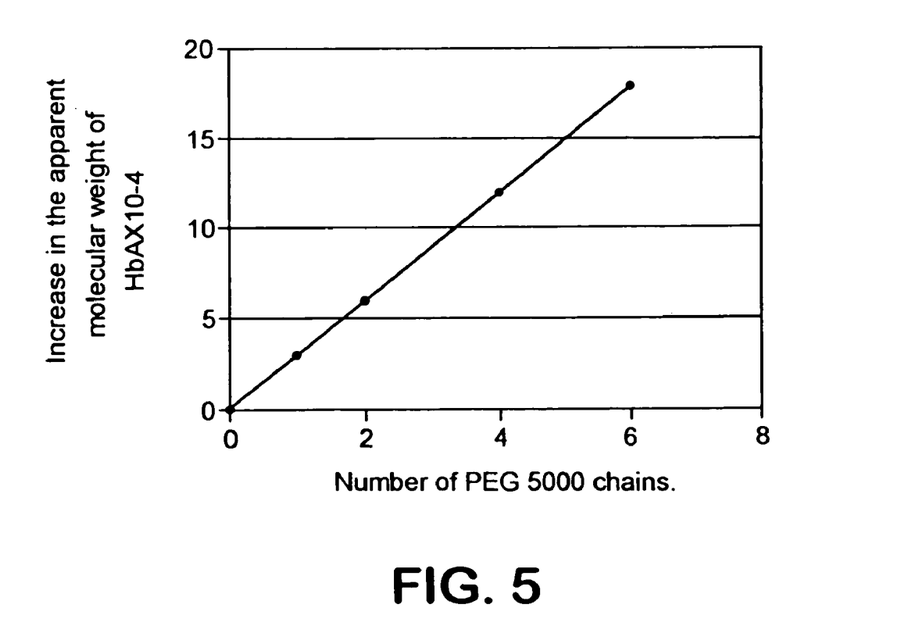
FIG. 5 is a graph showing the correlation between the apparent increase in the molecular size of HbA (as reflected by size exclusion chromatography) resulting from its amidation with the glycine ester of PEG-5000. HbA was amidated in the presence of 10, 25 and 50 mM EDC to determine the elution positions for HbA containing two, four and six copies of PEG-5000 chains per tetramer.

The progressive decrease in the retention times of HbA on amidation with the glycine ester of PEG-5000 as the concentration of EDC (water soluble carbodimide) used in the amidation mixture increases therefore reflects the correlation of the number of PEG-5000 chains with the apparent increase molecular size. 10 to 15 mM EDC reaction product predominantly containing two PEG-5000 chains elutes around 50 min, and represents molecular size corresponding to that of octameric form of HbA. The primary product generated in the presence of 25 mM EDC elutes around 47 minutes and this product corresponds to the molecular size of a hemoglobin dodecamer. The major product present in the 50 mM EDC amidated sample elutes around 44 minutes and thus corresponds closely to molecular size of hexadecameic HbA. The correlation of the number of PEG-5000 chains expected to be present in the major product of each of the amidated sample with the calculated apparent increase in the molecular size of HbA is shown in FIG. 5. There is a linear correlation between the increase in the hydrodynamic volume of the surface decorated HbA and the number of PEG-chains introduced onto the protein. (FIG. 5). A mass of 10,000 dalton of PEG conjugated on to the surface of Hb increased molecular size of Hb as much as one molecule of teramric HbA, 64,000 dalton (nearly six times the actual molecular size of PEG).

The results of the above study lead us to conclude that there is a linear correlation with the number of PEG-5000 chains on the tetramer and the increase in the apparent molecular size of HbA as the molecule is loaded up to 6 to eight PEG-5000 chains.

The possibility of decorating Hb with more than six to eight PEG-5000 chains has also been attempted to establish whether this linear correlation is true beyond the six to eight PEG-5000 chains as well. The thiolation mediated maleimide chemistry based PEGalation, as described in U.S. Pat. No. 5,585,484, was used to increase the extent of the PEGalation of Hb. Though we could increase the extent of thiolation through this procedure, the molecular size of the product did not change considerably. Thus, it appears that about six chains of PEG-5000 per tetramer represents the limiting number for surface decoration using PEG-5000 chains for which a reasonably direct correlation exists between the mass of PEG-chains introduced on to Hb and the apparent molecular size. Though the number of thiol groups that can be introduced onto Hb increased when the amount of the thiolating reagent (iminothiolane) was increased from 10-fold molar excess to 40-fold molar excess, subsequent PEGalation by maleidophenyl PEG-5000 on the Hb molecule appears to be very inefficient because once it carries six to eight PEG-5000 chains, there appears to be resistance to the attachment of additional PEG-chains even though the Hb has been thiolated to carry additional thiol groups to facilitate the PEGalation. The subsequent PEGalation thus appears to proceed very slowly, and the concomitant increase in the molecular size is very limited. The elution pattern also suggests that, as the extent of thiolation increases, the product generated becomes more and more heterogeneous. Thus a molecule of Hb with six to eight chains of PEG-5000, appears to be experiencing a 'crowding influence' which decreases the chances of adding additional PEG-chains on to the surface of HbA. Also, these newly added PEG-chains contribution toward an increase in the apparent molecular size appears to be very marginal.

Figure 8:
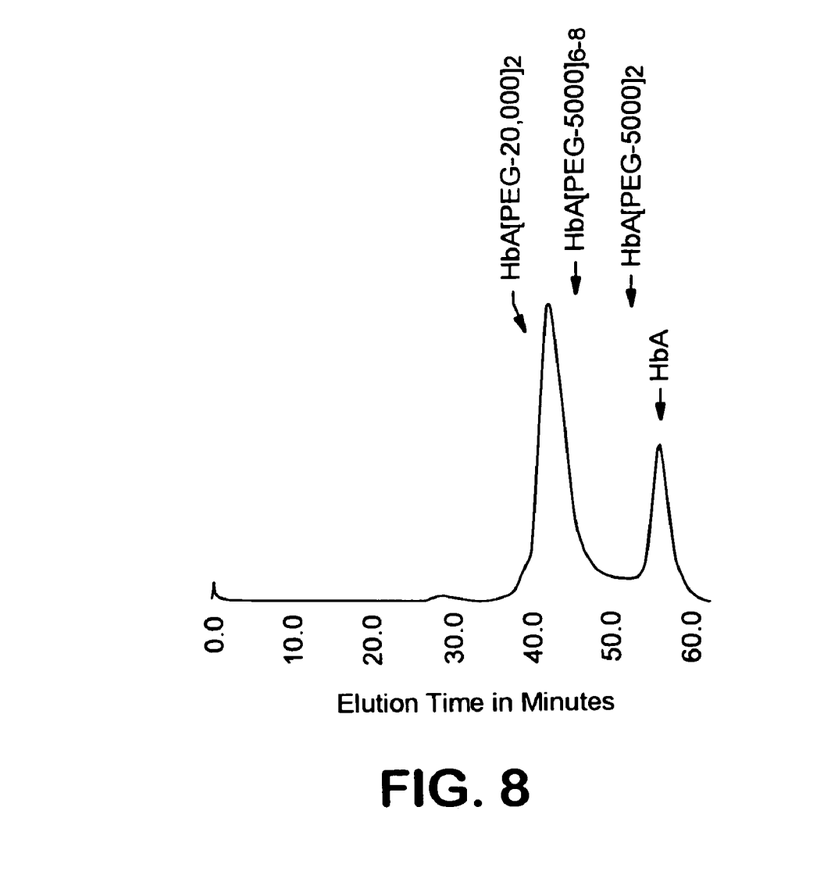
FIG. 8 is a graph representing the elution profile of HbA reacted with PEG-20,000 maleimide on Superose®-12 columns. The elution position of samples of HbA decorated with PEG-5000 is indicated.

An alternate approach of increasing the mass of PEG conjugated onto the surface of Hb is to use PEG-chains of higher mass. For example, instead of attaching 8 copies of maleidophenyl PEG-5000 on to the tetramer, one could attach two copies of maleidophenyl PEG-20,000 at the two Cys-93(β). The two preparations will have nearly the same total amount of PEG per tetramer. HbA carrying two PEG-20,000 chains on Cys-93(β), was thus prepared using maleidophenyl PEG-20,000. This species of Hb with a total PEG-mass of 40,000 dalton, elutes at a position earlier to that of the species of Hb that carry six to eight PEG-5000 chains per tetramer (FIG. 8). As noted earlier, the latter position corresponds to that of the hexadecameric species of HbA. Thus, the apparent molecular size of Hb(PEG-20,000)$_2$ is larger than that of hexadecameric species of HbA. We have obtained similar results with the reductive alkylation of Hb with PEG-20,000 propionaldehyde. The reaction has generated products of Hb that exhibited a molecular sieve chromatographic pattern comparable to that of the species that carry PEG-20,000 on the two Cys-93(β). This again supports the conclusion that the apparent increase in the molecular size is dictated by the molecular mass of PEG-chains attached to the surface of protein and not on where it is attached.

Therefore, the present study supports the conclusion that the most efficient approach for increasing the apparent molecular size of a protein by PEGalation is to attach lower number of longer PEG-chains than larger number of shorter PEG-chains.

EXAMPLE 5

Reaction of Mixed Disulfide of HbA and Dithiopyridine

HbA (0.5 mM) in phosphate buffered saline, pH 7.4 is incubated at room temperature with a 4 fold molar excess of dithiopyridine for two hours and the reaction mixture is gel filtered though a column of Sephadex® G-25 equilibrated with phosphate buffered saline. The mixed disulfide of Hb with dithiopyridine is formed in nearly quantitative yields as reflected by isoelectric focusing analysis. This modified Hb is then subjected to surface decoration with maleidophenyl PEG-5000 in the presence of iminothiolane, under conditions where six to eight PEG-5000 chains are introduced with the control Hb, two of which are present at the two Cys-93(β) residues of HbA. The Cys-93(β) if the surface decorated Hb is regenerated by treating the mixed disulfide with small molecular weight thiols. With the mixed disulfide of pyridine and Hb, the number of PEG-chains introduced are therefore to be lower by two PEG-5000 chains per tetramer. Nonetheless, the hydrodynamic volume of the product generated is not very different from that of the product obtained with the unmodified Hb. A comparison of the extent of thiolation showed that the number of new thiols introduced into the protein is not influenced by the formation of a mixed disulfide at Cys-93(β). The results demonstrate that the elution profile of a sample of surface decorated HbA and that of the mixed disulfide of pyridine and HbA are very similar. The number of PEG-chains present in the sample of HbA PEGlated with a ten fold molar excess of iminothiolane are more than enough for it to give an apparent molecular size higher than 256,000 daltons. This suggests that after attaining an apparent molecular size higher than 256,000 daltons, the propensity of additional PEG-chains to increase the apparent molecular size of Hb is very little. Thus, the crowding effect suggested in Example 4 with reference to the adding more than six to eight PEG chains a may be responsible for this observation as well.

In view of the above, it will be seen that the several advantages of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

What is claimed is:

1. A hemoglobin comprising a polyalkylene glycol, wherein the polyalkylene glycol is polypropylene glycol or polyethylene glycol (PEG), and wherein the polyalkylene glycol is covalently bonded to the hemoglobin at the α-amino of a Val-1(β).

2. The hemoglobin of claim 1, wherein the polyalkylene glycol is a PEG, and the hemoglobin is hemoglobin A.

3. The hemoglobin of claim 1, wherein the polyalkylene glycol is a PEG, and the hemoglobin further comprises a second PEG wherein the second PEG is covalently bonded to the hemoglobin at the α-amino of a Val-1(α).

4. The hemoglobin of claim 1, wherein the polyalkylene glycol is a PEG, and the PEG does not crosslink the hemoglobin intramolecularly or intermolecularly.

5. The hemoglobin of claim 1, wherein the polyalkylene glycol is a PEG, and the PEG intramolecularly crosslinks the hemoglobin.

6. The hemoglobin of claim 1, wherein the polyalkylene glycol is a PEG, and the PEG intermolecularly crosslinks the hemoglobin with a second hemoglobin.

7. The hemoglobin of claim 1, wherein the polyalkylene glycol is a PEG, and at least 4 PEGs are bonded to the hemoglobin at α-amino moieties.

8. The hemoglobin of claim 4, wherein the hemoglobin is hemoglobin A (HbA) bound with one or more PEG molecules, wherein the HbA-PEG has the formula wherein p is an integer from 2 to 6, q is 1 or 2, n is an integer from about 125 to about 500, m is an integer from 1 to 10, and R is selected from the group consisting of OH, OCH$_3$, CH$_2$OH, CH$_2$OCH$_3$, CH$_2$CH$_2$OH, and CH$_2$CH$_2$OCH$_3$.

9. The hemoglobin of claim 8, wherein q is 1, n is about 125, m is 1–4, and R is CH$_2$CH$_2$OCH$_3$.

10. The hemoglobin of claim 4, wherein the hemoglobin (Hb) is crosslinked by one or more PEG molecules, wherein the crosslinked Hb has the formula wherein Hb and Hb' are the same or different hemoglobin molecule, each p is independently an integer from 2 to 6, each q is 1 or 2, and n is an integer from about 15 to about 250.

11. The hemoglobin composition of claim 10, wherein q is 1, and Hb and Hb' are the same hemoglobin A tetramer.

12. The hemoglobin composition of claim 10, wherein q is 1, and Hb and Hb' are different hemoglobin A tetramers.

13. A composition comprising the hemoglobin of claim 1 in a pharmaceutically acceptable excipient.

14. A method of producing the hemoglobin comprising a polyalkylene glycol of claim 1, the method comprising incubating a hemoglobin with a polyalkylene glycol aldehyde and a borohydride under conditions and for a time sufficient for the polyalkylene glycol aldehyde to bond to the hemoglobin at the Val-1(β).

15. The method of claim 14, wherein the polyalkylene glycol is a PEG, the Hb is hemoglobin A, and the borohydride is sodium cyano borohydride.

16. A method of producing the hemoglobin comprising a PEG of claim 4, the method comprising incubating a hemoglobin with a PEG aldehyde and a borohydride under conditions and for a time sufficient for the PEG to bond to the hemoglobin at the Val-1(β), and wherein the PEG aldehyde has the formula wherein p is an integer from 2 to 6, q is 1 or 2, n is an integer from about 125 to about 500, and R is selected from the group consisting of OH, OCH$_3$, CH$_2$OH, CH$_2$OCH$_3$, CH$_2$CH$_2$OH, and CH$_2$CH$_2$OCH$_3$.

17. The method of claim 16, wherein q is 1, n is about 125, and R is CH$_2$CH$_2$OCH$_3$.

18. A method of producing the hemoglobin comprising a polyalkylene glycol of claim 1, wherein the PEG is covalently bonded to the hemoglobin at the α-amino of a Val-1(β) and crosslinks the hemoglobin intramolecularly or intermolecularly, the method comprising incubating the hemoglobin with a PEG aldehyde and a borohydride under conditions and for a time sufficient for the PEG to bond to the hemoglobin at the Val-1(β), wherein the PEG aldehyde has the formula wherein each p is independently an integer from 2 to 6, each q is independently 1 or 2, and n is an integer from about 15 to about 250.

19. A hemoglobin comprising a PEG, produced by the method of claim 15.

20. A hemoglobin comprising a PEG, produced by the method of claim 16.

21. A hemoglobin comprising a PEG, produced by the method of claim 18.

22. A composition comprising the hemoglobin of claim 19 in a pharmaceutically acceptable excipient.

* * * * *